United States Patent [19]

Kimura et al.

[11] 4,321,180

[45] Mar. 23, 1982

[54] ADHESIVE COMPOSITION

[75] Inventors: Kaora Kimura; Kyoji Sugiura, both of Nagoya, Japan

[73] Assignee: Toagosei Chemical Industry Co., Ltd., Tokyo, Japan

[21] Appl. No.: 209,253

[22] Filed: Nov. 21, 1980

[30] Foreign Application Priority Data

Dec. 24, 1979 [JP] Japan .................. 54/166932

[51] Int. Cl.³ .......................................... C08F 120/36
[52] U.S. Cl. ................................. 524/549; 526/270; 526/298; 524/555
[58] Field of Search ................. 260/29.6 WQ, 465.4; 526/270, 298

[56] References Cited

U.S. PATENT DOCUMENTS

| | | | |
|---|---|---|---|
| 2,784,215 | 3/1957 | Joyner | 526/298 |
| 3,465,027 | 9/1969 | Hawkins | 260/465.4 |
| 3,527,841 | 9/1970 | Wicker | 526/298 |
| 3,559,652 | 2/1971 | Banitt | 526/298 |
| 3,728,375 | 4/1973 | Coover | 260/465.4 |

OTHER PUBLICATIONS

Japanese Patent Application Kokai 130438/74.

Journal of the Japanese Society of Adhesion, vol. 4, No. 2, 1968, pp. 67–70.

Primary Examiner—Paul R. Michl
Attorney, Agent, or Firm—Cooper, Dunham, Clark, Griffin & Moran

[57] ABSTRACT

An adhesive composition consisting essentially of (A) an alkyloxyalkyl 2-cyanoacrylate represented by the formula,

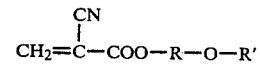

wherein R is an alkylene group having 2 to 4 carbon atoms and R' is an alkyl group having 2 to 6 carbon atoms, or tetrahydrofurfuryl 2-cyanoacrylate, (B) 300 to 2,000 ppm. of water, (C) a radical-polymerization inhibitor, and (D) an anionic-polymerization inhibitor. This adhesive composition is useful as an instant-setting adhesive for metals, plastics, rubbers, glass, wood and the like, is excellent in instant-setting properties, bond strength and storage stability, and neither emits an irritating odor nor causes whitening of the adherend surface.

12 Claims, No Drawings

ADHESIVE COMPOSITION

This invention relates to an adhesive comprising an ether-linkage-containing alkyl 2-cyanoacrylate, that is, an alkyloxyalkyl 2-cyanoacrylate, or tetrahydrofurfuryl 2-cyanoacrylate.

Since 2-cyanoacrylate adhesives generally become hardened instantaneously at room temperature by the moisture adsorbed in a minute quantity on the surface of an adherend, they are widely utilized in various industrial fields to bond metals, plastics, rubbers, glass, wood and the like.

However, conventional alkyl 2-cyanoacrylate adhesives have such defects that they emit an irritating odor and have a tendency to cause whitening, that is, such a phenomenon that white powder has been scattered on the adherend surface on application of the adhesive. Further, there is such a disadvantage that when the alkyl 2-cyanoacrylate adhesive has been cured, the resulting polymer per se is hard and brittle and lacks flexibility, and hence is insufficient in resistance to impact or flexure.

Among the known adhensives of the alkyl 2-cyanoacrylate type, those in actual use are methyl 2-cyanoacrylate, ethyl 2-cyanoacrylate, n-propyl 2-cyanoacrylate, n-butyl 2-cyanoacrylate and isobutyl 2-cyanoacrylate. Other alkyl 2-cyanoacrylate adhesives have never been put into practical use. These monomeric esters are all alike in chemical and physical properties and in adhesive activity. As a consequence, the adhesive activities of all the adhesive compositions comprising the above-noted alkyl esters resemble closely the adhesive activity of ethyl 2-cyanoacrylate adhesive which is used most widely at present. Higher alkyl 2-cyanoacrylates have been known to be lower in bonding speed and, in addition, in tensile, shear and impact strengths of the bonds. Further, it has been well known that conventional alkyl 2-cyanoacrylate adhesives have an irritating odor and a tendency to cause whitening.

A conventional process of manufacturing alkyl 2-cyanoacrylates has been publicly known in U.S. Pat. Nos. 2,721,858; 2,756,251; and 2,763,677. An alkyl cyanoacetate and formaldehyde are allowed to react at 50° to 90° in an organic solvent in the presence of a basic condensation catalyst such as piperidine or the like to form a condensation product and the water set free by the reaction is removed by distillation. After the removal of the solvent by distillation, the condensation product is depolymerized in the presence of phosphorus pentoxide ($P_2O_5$) at a temperature of 100° to 185° C. under a pressure of 15 mmHg or less to give an alkyl 2-cyanoacrylate. Although the above process is most generally used, there are specific processes. In one of said processes, tricresyl phosphate is added in depolymerizing the condensation product to dissolve the latter (U.S. Pat. No. 2,756,251). Japanese Patent Publication No. 14,567/63 discloses a process by which the condensation product of an alkyl cyanoacetate and formaldehyde is depolymerized after washing it with an aqueous acidic solution to yield an alkyl 2-cyanoacrylate monomer, chiefly monomeric methyl 2-cyanoacrylate.

The above production examples all pertain to those for alkyl 2-cyanoacrylate adhesives. The performance characteristics and the stability of a 2-cyanoacrylate adhesive are very sensitive to the contamination with minute amounts of moisture, basic or acidic substances. Accordingly, the process and conditions for manufacture and adhesive performance of a monomeric 2-cyanoacrylate must be properly selected for each kind of esters. It has been well known to those skilled in the art that it is impossible to apply the knowledge about the manufacturing conditions and properties of such conventional alkyl 2-cyanoacrylates as methyl 2-cyanoacrylate and ethyl 2-cyanoacrylate to the cases of other specific monomeric 2-cyanoacrylate esters.

The alkyloxyalkyl 2-cyanoacrylates of the general formula $CH_2=C(CN)-COO-R-O-R'$ wherein R is an alkylene radical of 2 to 4 carbon atoms and R' is an alkyl group of 2 to 6 carbon atoms, are known coupounds as disclosed in U.S. Pat. No. 2,784,215. However, if they are prepared by applying without modification the process and conditions for manufacture described in said patent specification or those for conventional alkyl 2-cyanoacrylates, the yield will be as low as 10 to 20% by weight owing to marked repolymerization of the alkyloxyalkyl 2-cyanoacrylate in the vapor phase during depolymerization; in fact, gas-chromatographic analysis revealed that the purity was as low as 70 to 80% and large amounts of an alkyloxyalkyl cyanoacetate and an alkyloxyalkanol were detected. Thus, in spite of purification by repeated distillation, the alkyloxyalkyl 2-cyanoacryaltes prepared by conventional processes do not exhibit sufficient adhesive characteristics and stability for the practical use.

Although the reason is yet to be elucidated, such phenomena are originated from the difference in chemical structure between the alkyloxyalkyl 2-cyanoacrylate and the conventional alkyl 2-cyanoacrylate. It is presumable that when a substance promoting an abnormal decomposition is present in the depolymerization mixture, abnormal decomposition of the alkyloxyalkyl group results in an ether, alcohol or the like, which accelerates the vapor phase-polymerization. Such accelerated polymerization plus its synergistic effect with autocatalysis due to the ether linkage of the alkyloxyalkyl 2-cyanoacrylate itself seem to give rise to the above behavior which is different from that of alkyl 2-cyanoacrylate.

A cyanoacetate seems also to be formed by the abnormal decomposition in this case. When a large amount of cyanoacetate is present in an alkyloxyalkyl 2-cyanoacrylate after depolymerization, it is very difficult to purify the latter by distillation because of the close proximity of the boiling points.

As described above, the alkyloxyalkyl cyanoacetate and alkyloxyalkanol which contaiminate the alkyloxyalkyl 2-cyanoacrylate during the preparation thereof adversely affect the performance characteristics of the adhesive such as bond strength, instant-setting ability, storage stability, etc. The present inventors have conducted further studies on the effect of the above contaminants and found that when the alkyloxyalkyl 2-cyanoacetate or alkyloxyalkanol content exceeds 5% by weight, the above-mentioned characteristics become rapidly deteriorated, thus rendering the adhesive substantially useless.

It has been further found that minute amounts of impurities affect the depolymerization to deteriorate the product quality.

The present inventors have consequently found that in order to render an alkyloxyalkyl 2-cyanoacrylate or tetrahydrofurfuryl 2-cyanoacrylate excellent in performance chracteristics and life (storage stability) as an adhesive, it is necessary, prior to the depolymerization step, to remove or consume by reaction minute amounts of impurities promoting the abnormal decomposition, which have been produced as by-products or incorporated in the condensation step while maintaining the viscosity of the condensation product within a certain range, whereby the subsequent depolymerization proceeds easily and a high quality adhesive may be obtained.

Further, it has been known that although excellent in adhesive performance, a high purity 2-cyanoacrylate is unsuitable for a long-term storage owing to its high activity and instability. The present inventors have, therefore, carried out extensive research to eliminate the said defect and, as a result, have found that an adhesive composition free from said defect is obtained by allowing the composition to contain a specified amount of water.

An object of this invention is to provide an adhesive composition comprising an alkyloxyalkyl 2-cyanoacrylate or tetrahydrofurfuryl 2-cyanoacrylate.

Another object of this invention is to provide an adhesive composition excellent in instant-setting ability, bond strength and storage stability, unsusceptible to whitening of the adherend surface, and free from an irritating odor.

Other objects and advantages of this invention will become apparent from the following description.

According to this invention, there is provided an adhesive composition consisting essentially of (A) an alkyloxyalkyl 2-cyanoacrylate represented by the general formula,

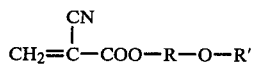

wherein R is an alkylene group having 2 to 4 carbon atoms and R' is an alkyl group having 2 to 6 carbon atoms, or tetrahydrofurfuryl 2-cyanoacrylate, (B) 300 to 2,000 ppm. of water, (C) a radical-polymerization inhibitor, and (D) an anionic-polymerization inhibitor.

The alkyloxyalkyl 2-cyanoacrylate and tetrahydrofurfuryl 2-cyanoacrylate employed in this invention must be of a high purity, and can be prepared by washing with water or an aqueous acidic solution the condensation product of formaldehyde with an alkyloxyalkyl cyanoacetate represented by the formula, NC—CH$_2$—CO$_2$—R—O—R', wherein R and R' are as defined above or tetrahydrofurfuryl cyanoacetate, while maintaining the viscosity of the condensation product within the range of from 1 to 500 centipoises, thereafter depolymerizing the washed condensation product and then distilling the depolymerization product.

The above method is described in more detail below.

An alkyloxyalkyl cyanoacetate of the formula, NC—CH$_2$—CO$_2$—R—O—R', or tetrahydrofurfuryl 2-cyanoacetate is allowed to condense with formaldehyde in the presence of 0.01 to 10 mole %, based on said cyanoacetate, of a basic catalyst, that is, a basic compound such as an amine, e.g. piperidine, sodium hydroxide, potassium hydroxide, or an alkali metal alkoxide. The molar ratio of the alkyloxyalkyl or tetrahydrofurfuryl cyanoacetate to formaldehyde in the reactant mixture is preferably 1:0.7–1.3, more preferably 1:1.

A solvent is usually used in the condensation reaction. As the solvents, there may be used inert solvents such as benzene, toluene, ethyl alcohol, chloroform, trichloroethylene, tetrahydrofuran, water and the like. It is also possible to use a binary solvent, such as a mixture of water and toluene. The amount of the solvent used is preferably in the range of 50 to 300 ml per mole of the alkyloxyalkyl or tetrahydrofurfuryl cyanoacetate.

The condensation reaction is carried out preferably at a temperature of 30° to 150° C., more preferably at a reflux temperature of 50° to 100° C. A reaction time of from several hours to 24 hours is suitable. The condensation product of an alkyloxyalkyl or tetrahydrofurfuryl cyanoacetate with formaldehyde is a high-viscosity liquid or a brittle solid containing a trace to small amounts of the condensation catalyst, unreacted reactants, an acid, an alcohol, by-products of the reaction, lower condensation products, and the like.

As previously described, no success is obtained by depolymerizing the above condensation product as such in the presence of a depolymerization catalyst such as P$_2$O$_5$ or the like. The condensation product should be washed with an aqueous acidic solution or water, and, although the reason is not clarified, it is essential, during the washing treatment, to maintain the viscosity of the condensation product within the range of 1 to 500, preferably 20 to 250, centipoises. When a condensate having a viscosity outside the said range is washed, the washed product is difficult to depolymerize in the next step, or even if depolymerization is possible, no good quality adhesive is obtained. The maintenance of the viscosity of the condensation product within the range of 1 to 500, preferably 20 to 250, centipoises can be achieved by elevating the temperature up to about 100° C. or by employing in the condensation step a predetermined amount of a solvent, for example, an aromatic hydrocarbon such as benzene, toluene or the like; a ketone such as methyl ethyl ketone, methyl isobutyl ketone, cyclohexanone or the like; an ester such as ethyl acetate, butyl acetate or the like, a chlorohydrocarbon such as trichloroethylene, dichloroethane or the like; an ether such as methyl ethyl ether or the like or a furan compound such as tetrahydrofuran, or by diluting the condensation product with said solvent.

The washing is carried out at a temperature in the range of 0° to 100° C. The acids used in the washing treatment include those which show acidity in aqueous solution, such as sulfuric acid, hydrochloric acid, phosphoric acid, p-toluenesulfonic acid, benzenesulfonic acid, formic acid, acetic acid and the like. The concentration of the acid is preferably in the range of 0.01 to 5% by weight.

The condensation product washed under the above-mentioned conditions is depolymerized in a conventional manner. That is to say, the depolymerization is effected by heating the condensation product at a temperature in the range of 100° to 250° C., preferably 140° to 200° C. in vacuo in the presence of a depolymerization catalyst such as phosphorus pentoxide, phosphoric acid, or polyphosphoric acid, whereby a crude monomer is obtained in a high yield.

On redistilling the crude monomer, there is obtained a high quality alkyloxyalkyl or tetrahydrofurfuryl 2-cyanoacrylate.

In the above case, only by the process by which the condensation product is washed while maintaining its viscosity within the range of 1 to 500, preferably 20 to 250, centipoises, there is obtained an alkyloxyalkyl or tetrahydrofurfuryl 2-cyanoacrylate having an unreacted 2-cyanoacetate content of 5% by weight or less, preferably 2% by weight or less, most preferably 1% by weight or less, an alcohol content of 5% by weight or less, preferably 2% by weight or less, most preferably 1% by weight or less, and a low moisture content.

The alkyloxyalkyl 2-cyanoacrylates used in this invention include, for example, 2-ethoxyethyl 2-cyanoacrylate, 2-propoxyethyl 2-cyanoacrylate, 2-butoxyethyl 2-cyanoacrylate, 2-hexyloxyethyl 2-cyanoacrylate, 2-ethoxybutyl 2-cyanoacrylate, 2-amyloxyethyl 2-cyanoacrylate, and the like.

It has heretofore been considered that the smaller the moisture content in the alkyl 2-cyanoacrylate, the better. U.S. Pat. No. 3,728,375 discloses that when the monomeric 2-cyanoacrylate is prepared in a production apparatus which has been dried the moisture content in the monomer obtained becomes 50 to 200 ppm., the setting time is short (in other words, the bonding speed is high), and the storage stability is excellent. The rapid deterioration in adhesive performance of a 2-cyanoacrylate having a moisture content exceeding 200 ppm. during storage is due to an increase in acidic substance content by decomposition of the 2-cyanoacrylate caused by the water molecules contained therein. It is also known, as is clear from Japanese Patent Application Kokai (Laid-Open) No. 130,438/74, that an alkyl 2-cyanoacrylate of a moisture content of 5,000 to 10,000 ppm. has a short setting time and an excellent storage stability. Therefore, a conventional alkyl 2-cyanoacrylate adhesive has been considered to exhibit excellent adhesive performance characteristics when its moisture content is in the range of from 50 to 200 ppm. or in the range of 5,000 to 10,000 ppm., whereas when the moisture content is in the intermediate range of 200 to 5,000 ppm., the storage stability becomes lower, the performance characteristics deteriorate rapidly during storage, and the adhesive activity becomes also low.

The alkyloxyalkyl or tetrahydrofurfuryl 2-cyanoacrylate obtained as described above is of a high purity and is excellent in bonding performance, but owing to its high activity and low stability, it is unsuitable for the long-term storage.

The present inventors have carried out extensive research to ameliorate the adhesive performance as well as the storage stability of the alkyloxyalkyl cyanoacrylate and have, as a result, found that quite contrary to the case of conventional alkyl 2-cyanoacrylate, an alkyloxyalkyl 2-cyanoacrylate monomer exhibits a high activity short setting time, high bond strength and optimum storage stability when the monomer has a moisture content in the range of 300 to 2,000 ppm., preferably 400 to 1,500 ppm.

In the case of this invention, when the moisture content in the alkyloxyalkyl 2-cyanoacrylate or tetrahydrofurfuryl 2-caynoacrylate is less than 300 ppm., the storage stability of the adhesive is markedly low. Although the reason therefor is not entirely understood, the low storage stability seems to result from the ether linkage of the monomer. The ether linkage has a tendency to cause or promote free-radical or anionic polymerization of the 2-cyanoacrylate, and when the moisture content in the adhesive composition becomes less than 300 ppm., the adhesive composition becomes too active and the viscosity thereof is consequently increased with the lapse of time during storage until the hardening occurs finally. Further, when the adhesive composition has a moisture content of less than 300 ppm., wetting of the adherend surface with the adhesive composition becomes markedly inferior, the penetration of the composition into the adherend surface layer becomes also low, and the bond strength thereof tends to decrease.

On the other hand, when the moisture content exceeds 2,000 ppm., the storage stability decreases, and the setting time becomes remarkably long with the lapse of time. At the same time, the bonding strength decreases, so that the composition has lost completely its function as an instant-setting adhesive. If the moisture content is further increased to reach more than 5,000 ppm., the viscosity of the adhesive composition, of course, increases in a relatively short period of time until the composition hardens finally.

It is well-known from U.S. Pat. Nos. 3,728,375 and 3,465,027 that with the decrease in moisture content, the alkyl 2-cyanoacrylate becomes better in adhesive performance and in storage stability, and particularly, a moisture content of 50 to 200 ppm. is preferable. Quite contrary to the conventional knowledge, in the case of the alkyloxyalkyl 2-cyanoacrylate or tetrahydrofurfuryl 2-cyanoacrylate of this invention, it is necessary that the moisture content be in the range of 300 to 2,000 ppm., preferably 400 to 1,500 ppm. If the moisture content falls outside the said range, it is difficult to obtain an adhesive satisfactory in both storage stability and adhesive activity.

As described previously, the alkyloxyalkyl 2-cyanoacrylate of this invention is represented by the general formula,

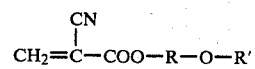

wherein R is an alkylene radical of 2 to 4 carbon atoms and R' is an alkyl group having 2 to 6 carbon atoms.

A 2-cyanoacrylate having the above formula wherein R has one carbon atom cannot be employed in this invention because of its instability and susceptibility to hydrolysis with a minute amount of moisture, whereas a 2-cyanoacrylate having 5 or more carbon atoms in R is difficult to obtain in a highly pure form, so that an adhesive inferior in both adhesion performance and stability will result. A 2-cyanoacrylate having one carbon atom in R' cannot be freed from malodor, is of low stability (this stability is difficult to improve even by the control of moisture content), and gives an adhesive inferior in adhesive performance, particularly in water resistance and durability. When R' has 7 or more carbon atoms, a high-purity monomer is difficult to obtain and the adhesive obtained therefrom is deficient in performance characteristics and stability.

The adhesive composition of this invention comprising an alkyloxyalkyl 2-cyanoacrylate or tetrahydrofurfuryl 2-cyanoacrylate should contain an anionic-polymerization inhibitor to protect the composition from viscosity increase and gelation caused by the moisture during storage. Specific examples of the inhibitors include $SO_2$, $SO_3$, $NO$, $NO_2$, $HCl$, $H_3PO_4$, esters of hydrogen phosphate, aromatic sulfonic acids, alkylsulfonic acids, propanesultone, trifluoromethanesulfonic acid, perfluoroalkylcarboxylic acids and the like. These are used in an amount of preferably 1 to 10,000 ppm., more preferably 5 to 1,000 ppm.

Further, the adhesive composition of this invention must contain a radical-polymerization inhibitor. This is for preventing the composition from radical polymerization during storage and is, at the same time, an antioxidant to inhibit the formation or accumulation of peroxides caused by the ether linkage of the alkyloxyalkyl 2-cyanoacrylate or tetrahydrofurfuryl 2-cyanoacrylate.

Typical examples of the radical-polymerization inhibitors are aryl alcohols such as phenol, cresols, hydroquinone, benzoquinone, α-naphthol, β-naphthol, catechol, pyrogallol, Bisphenol-A, Bisphenol-S, 2,6-di-tert-butylphenol, 2,6-di-tert-butylcresol, 2,2'-methylene-bis(4-methyl-6-tert-butylphenol), 4,4'-butylidene-bis(3-methyl-6-tert-butylphenol), 4,4'-thiobis(3-methyl-6-tert-butylphenol), 4,4'-thiobis(3-methyl-6-tert-butylphenol), hydroquinone monomethyl ether, 2-hydroxybenzophenone, phenylsalicylic acid, 1,3,5-trimethyl-2,4,6-tris(3,5-di-tert-butyl-4-hydroxybenzyl)benzene, and the like. These are used in an amount of preferably 1 to 10,000 ppm., more preferably 10 to 5,000 ppm.

Conventional alkyl 2-cyanoacrylates are not liable to peroxide formation and, hence, do not necessarily require a radical-polymerization inhibitor. However, in the case of the alkyloxyalkyl 2-cyanoacrylate or tetrahydrofurfuryl 2-cyanoacrylate of this invention, the methylene radical involved in an ether linkage is liable to peroxide formation so that it becomes necessary to inhibit the peroxide formation or to decompose the formed peroxide by the addition of an antioxidant of the aromatic alcohol type.

The adhesive composition of this invention may have incorporated thereinto, if necessary, thickners, plasticizers, dyes, pigments, solvents, diluents, perfumes, etc.

The adhesive composition of this invention is very useful as an instant-setting adhesive which is hardly susceptible to whitening, is free from irritating odor, and is more flexible than conventional alkyl 2-cyanoacrylates.

The invention is illustrated below with reference to Examples which are merely illustrative and not limitative. In the Examples, all percentages and parts are by weight unless otherwise specified.

EXAMPLE 1

Into a four-necked flask provided with a stirrer, a thermometer, a water trap and a dropping funnel were charged 60 parts of paraformaldehyde, 200 parts of toluene and 0.2 part of piperidine. To the mixture was added dropwise at 80° to 90° C. with stirring 314 parts of 2-ethoxyethyl cyanoacetate. After the completion of the dropwise addition, the mixture was allowed to react under reflux, while removing the water formed by the reaction, until all of the theoretical amount of water had been distilled out. The reaction mixture was then cooled down to room temperature. To the resulting condensation mixture having a viscosity of 200 centipoises was added 300 parts of a 1% aqueous solution of p-toluenesulfonic acid. The mixture was shaken at 70° C., and then allowed to stand, upon which it separated into two layers. The oil layer thereof was taken out.

The oil layer was distilled under reduced pressure to remove the toluene. To the condensation product left in the pot were added 3 parts of each of phosphorus pentoxide and hydroquinone. The mixture was subjected to depolymerization by heating at 150° to 200° C. under a pressure of 3 to 5 mmHg to obtain 266 parts (83% yield) of a crude monomer. The crude monomer had a purity of 96.8% and contained 0.50% of 2-ethoxyethyl 2-cyanoacetate, 1.20% of 2-ethoxyethanol, 0.15% of moisture, and 1.3% of other impurities in total.

After the addition of 0.5% of phosphorus pentoxide and 0.5% of hydroquinone to the crude monomer, the resulting mixture was redistilled to obtain 220 parts of 2-ethoxyethyl 2-cyanoacrylate containing 0.48% of 2-ethoxyethyl cyanoacetate, 0.50% of 2-ethoxyethanol, and 0.05% of moisture, the boiling point and the purity having been 100°-102° C./3 mmHg and 98.8%, respectively. An adhesive composition was prepared by adding to the above monomer 50 ppm. of $SO_2$ and 100 ppm. of hydroquinone. On the other hand, water was added to the ethoxyethyl 2-cyanoacrylate containing 0.05% (500 ppm.) of moisture, to prepare adhesive compositions containing, respectively, 1,000 ppm., 1,500 ppm., 1,800 ppm. (these are Examples of this invention), 2,500 ppm. and 5,000 ppm. (these are Comparative Examples) of moisture based on the weight of the ethoxyethyl 2-cyanoacrylate.

Further, an adhesive composition containing 200 ppm. of moisture was prepared by drying the ethoxyethyl 2-cyanoacrylate containing 0.05% of moisture with a molecular sieve (3 Å) (Comparative Example).

USE EXAMPLES 1 TO 4 AND COMPARATIVE USE EXAMPLES 1 TO 3.

The adhesive compositions of the Examples and the Comparative Examples obtained in Example 1 were tested for forced storage stability including the adhesive characteristics. The results obtained were as shown in Table 1. Each adhesive was placed in a polyethylene container, 2 ml in volume, and kept in a thermostat at 60° C. to examine the deterioration with the lapse of time. Fifty days of the forced deterioration correspond to about one year of allowing to stand at room temperature in the dark.

TABLE 1

| | Composition | | | Early-stage bonding performance | | After 30 days of forced deterioration | | | After 50 days of forced deterioration | | |
|---|---|---|---|---|---|---|---|---|---|---|---|
| | Moisture (ppm) | $SO_2$ (ppm) | Hydroquinone (ppm) | Setting time (sec.) | Tensile shear strength of bond (kg/cm²) | Setting time (sec.) | Tensile shear strength of bond (kg/cm²) | Viscosity | Setting time (sec.) | Tensile shear strength of bond (kg/cm²) | Viscosity |
| Use Example | | | | | | | | | | | |
| 1 | 500 | 50 | 200 | <2 | 160 | <2 | 150 | No change | <2 | 150 | No change |
| 2 | 1000 | 50 | 200 | <2 | 165 | <2 | 160 | No change | <2 | 150 | No change |
| 3 | 1500 | 50 | 200 | <2 | 160 | <2 | 160 | No change | <2 | 155 | No change |
| 4 | 1800 | 50 | 200 | <2 | 150 | <2 | 150 | No change | <2 | 140 | No change |
| Comparative Use Example | | | | | | | | | | | |
| 1 | 2500 | 50 | 200 | 3 | 125 | >120 | 50 | Viscosity increase | >300 | — | Almost gelled |
| 2 | 5000 | 50 | 200 | 5 | 100 | >300 | — | Almost | — | — | Gelled |

TABLE 1-continued

| | Composition | | | Early-stage bonding performance | | After 30 days of forced deterioration | | | After 50 days of forced deterioration | | |
|---|---|---|---|---|---|---|---|---|---|---|---|
| | Moisture (ppm) | SO₂ (ppm) | Hydroquinone (ppm) | Setting time (sec.) | Tensile shear strength of bond (kg/cm²) | Setting time (sec.) | Tensile shear strength of bond (kg/cm²) | Viscosity | Setting time (sec.) | Tensile shear strength of bond (kg/cm²) | Viscosity |
| 3 | 200 | 50 | 200 | <2 | 130 | 5 | 150 | gelled Viscosity increase | — | — | Gelled |

Note
(1) Tensile shear strength of bond: JIS K 6850; steel to steel bond.
(2) Setting time: To a test pice of NBR, 5 × 20 (bonding surface) × 30 mm, was applied one drop of the adhesive composition and another test piece of the identical size was butted thereagainst, and the assembly was allowed to stand for a predetermined period of time, after which a load of 5 kg was applied thereto. If the bonded surfaces were not peeled thereby, said predetermined period is expressed as setting time. A setting time of "<2" to "<5" means that the adhesive is highly active and posseses sufficient properties for an instant-setting adhesive.

REFERENCE EXAMPLE 1

All of the adhesive compositions used in Use Examples 1 to 4 were absolutely odorless and even after 50 days of forced deterioration (in a thermostat at 60° C.) no malodor or irritating odor was detected.

To test the whitening one drop of each of the adhesive compositions used in Use Examples 1 to 4 and, for comparison, one drop of a commercial adhesive composition comprising ethyl 2-cyanoacrylate was allowed to fall onto the approximately central part of the bottom of a cleaned Petri dish, after which the Petri dish was covered and allowed to stand at room temperature for 24 hours. The commercial adhesive composition showed whitening all over the dish, whereas the adhesive compositions of Use Examples 1 to 4 showed slight whitening only in the area where the drop of adhesive composition was allowed to fall.

EXAMPLE 2

2-Ethoxyethyl 2-cyanoacrylate prepared in the same manner as in Example 1 was incorporated with 50 ppm. of p-toluenesulfonic acid and 200 ppm. of hydroquinone monomethyl ether, both used as stabilizers, to prepare an adhesive composition containing 400 ppm. of moisture.

A polyethylene container and an aluminum tube, each 20 g in capacity, were both filled with 20 g of the above adhesive composition. To examine the storage stability, the filled containers were subjected to forced deterioration in a thermostat at 60° C. After 50 days, the adhesive composition in each of the containers showed good stability. To the contrary, an adhesive composition containing 200 or 3,000 ppm. of moisture showed gelation on the same test as above.

EXAMPLE 3

To the 2-ethoxyethyl 2-cyanoacrylate prepared in Example 1 were added, as stabilizers, 100 ppm. of SO₂ and 100 ppm. of hydroquinone followed by, as thickener, 3% of polymethyl methacrylate to increase the viscosity to about 100 centipoises. The moisture content of the resulting adhesive composition was 650 ppm. The tensile shear strength of bond of the composition was 160 kg/cm² which was the same as that of the above composition before addition of the thickener. The storage stability of the composition was as good as or better than that of an adhesive composition having a moisture content of 200 ppm. which was prepared from ethyl 2-cyanoacrylate containing 100 ppm. of SO₂ and 100 ppm. of hydroquinone by adding polymethyl methacrylate to increase the viscosity to 100 centipoises.

EXAMPLE 4

To a mixture of 60 parts of paraformaldehyde, 200 parts of toluene and 0.2 part of piperidine, while heating at 80° to 90° C., was added dropwise 338 parts of tetrahydrofurfuryl cyanoacetate (boiling point, 130° C./1 mmHg) prepared by esterifying cyanoacetic acid with tetrahydrofurfuryl alcohol, allowing the mixture to react. After completion of the dropwise addition, the mixture was further allowed to react under reflux for 4 hours while removing the by-product water by distillation to obtain a viscous condensation product. To the condensation product solution was added 200 parts of toluene to adjust the viscosity to 40 centipoises (20° C.). The resulting solution was washed with 100 parts of water.

The oil phase was separated and the toluene was removed therefrom by distillation under reduced pressure. The condensation product was admixed with 3 parts of phosphorus pentoxide and 3 parts of hydroquinone, and the mixture was subjected to depolymerization at 170° to 200° C. to obtain 224 parts of the crude monomer. The crude monomer was redistilled to yield tetrahydrofurfuryl 2-cyanoacrylate boiling at 108°–111° C./1.5 mmHg.

Elementary analysis:

| | C | H | N |
|---|---|---|---|
| Calcd. (%) | 59.66 | 6.12 | 7.73 |
| Found (%) | 59.62 | 6.03 | 7.89 |

This 2-cyanoacrylate contained 0.3% of tetrahydrofurfuryl cyanoacetate, 0.2% of tetrahydrofurfuryl alcohol and 0.09% (900 ppm.) of moisture.

A composition prepared by adding 20 ppm. of SO₂ and 200 ppm. of hydroquinone to the above 2-cyanoacrylate was an absolutely odorless clear liquid having a viscosity of 100 centipoises (20° C.). This adhesive composition showed a setting time of 10 seconds on NBR rubber, 30 seconds on steel and a tensile shear strength of bond of 180 kgf/cm² (NBR) and 330 kgf/cm² (steel). These performance characteristics were equivalent to those of a conventional ethyl 2-cyanoacrylate adhesive. Similar tests on ABS resin showed a setting time of 30 seconds. Upon testing of the tensile shear strength of bond, a failure occurred in the ABS resin itself.

EXAMPLE 5

2-Butyloxyethyl 2-cyanoacrylate was prepared in the same manner as in Example 1, except that butyloxyethyl 2-cyanoacetate was substituted for the 2-ethoxyethyl cyanoacetate. The 2-cyanoacrylate obtained contained 400 ppm. of moisture, 0.05% of 2-butyloxyethyanol and 0.3% of 2-butyloxyethyl cyanoacetate. To the above 2-cyanoacrylate was added 20 ppm. of $SO_2$. Adhesive compositions were prepared by adding an antioxidant as shown in Table 2 to the 2-cyanoacrylate.

USE EXAMPLES 5 TO 9 AND COMPARATIVE USE EXAMPLE 4

A polyethylene container (20 g capacity) was filled with 20 g of the adhesive composition prepared in Example 5, and subjected to the forced deterioration test at 60° C. The results were as shown in Table 2.

TABLE 2

| | | Initial | | After forced deterioration 60° C., 50 days | |
|---|---|---|---|---|---|
| | Aromatic phenol | Setting time (sec.) | Tensile shear strength of bond (kg/cm$^2$) | Setting time (sec.) | Tensile shear strength of bond (kg/cm$^2$) |
| Use Example No. 8 | Hydroquinone monomethyl ether (200 ppm.) | <2 | 135 | 3 | 105 |
| 9 | Catechol (100 ppm.) | <2 | 130 | 3 | 100 |
| 10 | 2,6-Di-tert-butyl-p-cresol (300 ppm.) | <2 | 130 | 4 | 100 |
| 11 | 2-Cyclohexylhydroquinone (500 ppm.) | <2 | 140 | 3 | 110 |
| 12 | α-Naphthol (500 ppm.) | <2 | 120 | 3 | 105 |
| Comparative Use Example No. 4 | None | <2 | 130 | 30 increase in viscosity | 50 |

What is claimed is:

1. An adhesive composition consisting essentially of (A) an alkyloxyalkyl 2-cyanoacrylate represented by the general formula,

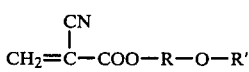

wherein R is an alkylene group having 2 to 4 carbon atoms and R' is an alkyl group having 2 to 6 carbon atoms, or tetrahydrofurfuryl 2-cyanoacrylate, (B) 300 to 2,000 ppm. of moisture, (C) a radical-polymerization inhibitor, and (D) an anionic-polymerization inhibitor.

2. An adhesive composition according to claim 1, wherein the alkyloxyalkyl 2-cyanoacrylate or tetrahydrofurfuryl 2-cyanoacrylate contains 2% by weight or less of an unreacted cyanoacetate and 2% by weight or less of an alcohol.

3. An adhesive composition according to claim 2, wherein the unreacted cyanoacetate content is 1% by weight or less and the alcohol content is 1% by weight or less.

4. An adhesive composition according to any of claims 1 to 3, wherein the alkyloxyalkyl 2-cyanoacrylate is 2-ethoxyethyl 2-cyanoacrylate, 2-propoxyethyl 2-cyanoacrylate, 2-butoxyethyl 2-cyanoacrylate, 2-hexyloxyethyl 2-cyanoacrylate, 2-ethoxybutyl 2-cyanoacrylate or 2-amyloxyethyl 2-cyanoacrylate.

5. An adhesive composition according to claim 1, wherein the moisture content is 400 to 1,500 ppm.

6. An adhesive composition according to claim 1, wherein the anionic-polymerization inhibitor is contained in a concentration of 1 to 10,000 ppm.

7. An adhesive composition according to claim 1, wherein the anionic-polymerization inhibitor is contained in a concentration of 5 to 1,000 ppm.

8. An adhesive composition according to claim 1, 5 or 6, wherein the anionic-polymerization inhibitor is $SO_2$, $SO_3$, NO, $NO_2$, HCl, $H_3PO_4$, a hydrogenphosphate ester, an aromatic sulfonic acid, an alkylsulfonic acid, propanesultone, trifluoromethanesulfonic acid, or a perfluoroalkylcarboxylic acid.

9. An adhesive composition according to claim 1 or 6, wherein the radical-polymerization inhibitor is contained in a concentration of 1 to 10,000 ppm.

10. An adhesive composition according to claim 1 or 7, wherein the radical-polymerization inhibitor is contained in a concentration of 10 to 5,000 ppm.

11. An adhesive composition according to claim 1, wherein the radical-polymerization inhibitor is an aryl alcohol.

12. An adhesive composition according to claim 11, wherein the aryl alcohol is phenol, a cresol, hydroquinone, benzoquinone, α-naphthol, β-naphthol, catechol, pyrogallol, Bisphenol-A, Bisphenol-S, 2,6-di-tert-butylphenol, 2,6-di-tert-butylcresol, 2,2'-methylenebis(4-methyl-6-tert-butylphenol), 4,4'-butylidenebis(3-methyl-6-tert-butylphenol), 4,4'-thiobis(3-methyl-6-tert-butylphenol), 4,4'-thiobis(3-methyl-6-tert-butylphenol), hydroquinone monomethyl ether, 2-hydroxybenzophenone, phenylsalicyclic acid, or 1,3,5-trimethyl-2,4,6-tris(3,5-di-tert-butyl-4-hydroxybenzyl)benzene.

* * * * *

UNITED STATES PATENT AND TRADEMARK OFFICE
CERTIFICATE OF CORRECTION

PATENT NO. : 4,321,180
DATED : March 23, 1982
INVENTOR(S) : KAORU KIMURA ET AL

It is certified that error appears in the above—identified patent and that said Letters Patent are hereby corrected as shown below:

COVER PAGE, the name of the first inventor should correctly read -- KAORU KIMURA --

Signed and Sealed this

Eighth Day of March 1983

[SEAL]

Attest:

GERALD J. MOSSINGHOFF

Attesting Officer   Commissioner of Patents and Trademarks